United States Patent [19]

Smith, Jr. et al.

[11] Patent Number: 4,937,363

[45] Date of Patent: Jun. 26, 1990

[54] FALLING FILM ALUMINOXANE PROCESS

[75] Inventors: Gerald Z. Smith, Jr., Francisville; Scott A. Bottelberghe, Port Allen, both of La.

[73] Assignee: Ethyl Corporation, Richmond, Va.

[21] Appl. No.: 313,075

[22] Filed: Feb. 21, 1989

[51] Int. Cl.$^5$ ................................................. C07F 5/06
[52] U.S. Cl. ........................................................ 556/179
[58] Field of Search ........................................... 556/179

[56] References Cited

U.S. PATENT DOCUMENTS

| | | | |
|---|---|---|---|
| 2,744,074 | 5/1956 | Theobald | 556/179 X |
| 3,184,490 | 5/1965 | Davison | 556/179 X |
| 3,220,797 | 11/1965 | Lester | 556/179 X |
| 3,454,615 | 7/1969 | Tani et al. | 556/179 |
| 3,655,329 | 4/1972 | Shih et al. | 556/179 X |
| 4,544,762 | 10/1985 | Kaminsky et al. | 556/179 |
| 4,665,208 | 5/1987 | Welborn, Jr. et al. | 556/179 |
| 4,730,071 | 3/1988 | Schoenthal et al. | 556/179 |
| 4,730,072 | 3/1988 | Schoenthal et al. | 556/179 |

FOREIGN PATENT DOCUMENTS

| | | | |
|---|---|---|---|
| 0279586 | 8/1988 | European Pat. Off. | 556/179 |
| 0158792 | 9/1982 | Japan | 556/179 |

*Primary Examiner*—Paul F. Shaver
*Attorney, Agent, or Firm*—Joseph D. Odenweller

[57] ABSTRACT

Alkylaluminoxanes are made by conducting a solution of an alkylaluminum (e.g. trimethyl aluminum) in an inert solvent to the top of an upright hollow column and allowing the solution to flow as a thin film down the inner surface of the column while passing a wet inert gas (e.g. nitrogen) up through the column such that the wet inert gas contacts the thin falling film of alkyl aluminum solution forming alkylaluminoxane.

19 Claims, 1 Drawing Sheet

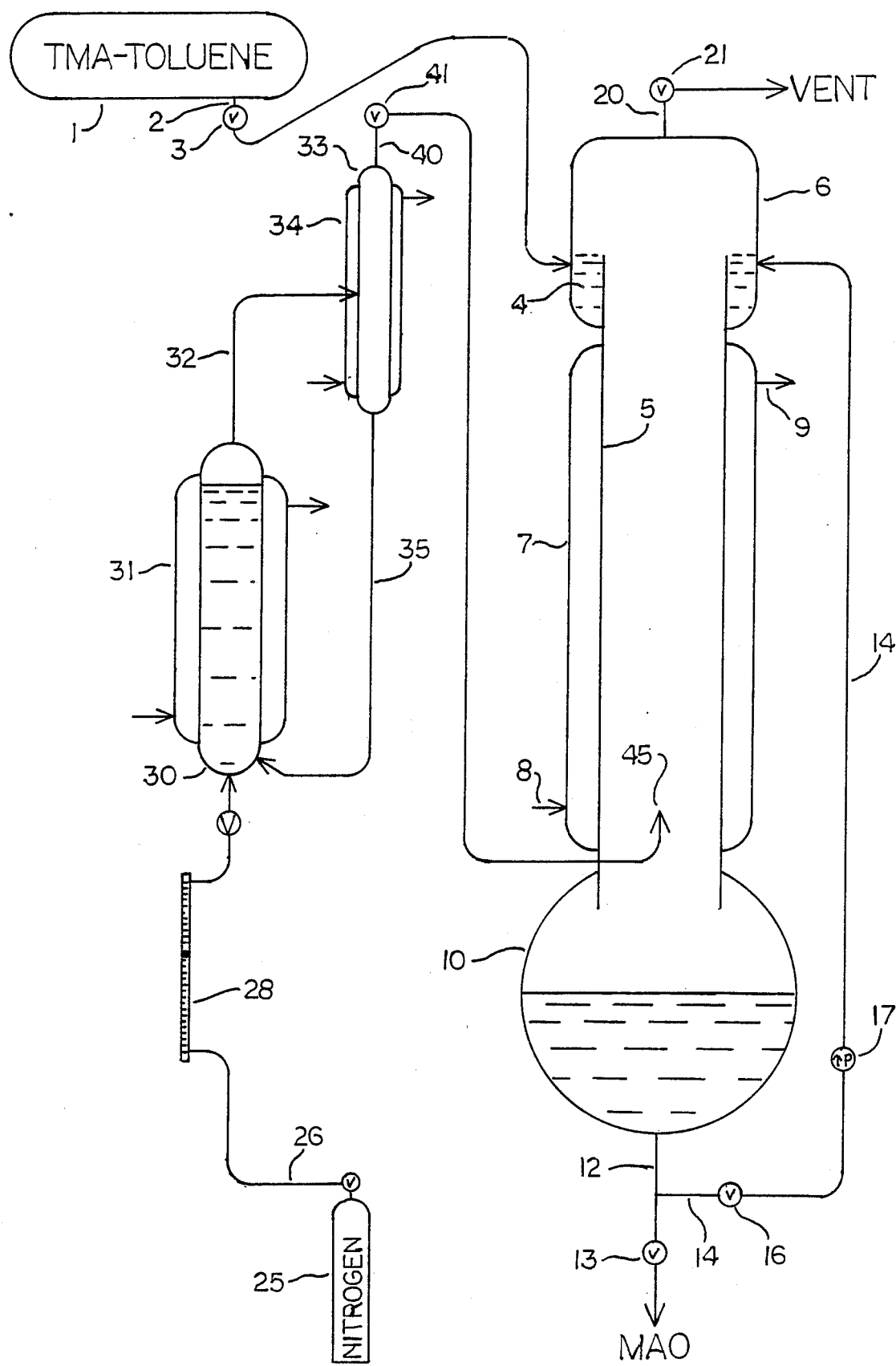

4,937,363

FALLING FILM ALUMINOXANE PROCESS

BACKGROUND

Vandenberg, U.S. Pat. No. 3,219,591, reported the catalytic activity of compounds formed by the reaction of trialkyl aluminum with limited amounts of water in the polymerization of epichlorohydrin and other oxiranes. Shortly thereafter Manyik et al., U.S. Pat. No. 3,242,099, reported the use of aluminoxanes, made by reacting 0.85–1.05 moles of water with hydrocarbyl aluminum compounds such as triisobutyl aluminum, as co-catalysts with certain transition metal compounds in the polymerization of mono-unsaturate α-olefins; e.g. ethylene, propylene. Isobutylaluminoxane was made by adding an equal mole quantity of water to a heptane solution of triisobutyl aluminum.

Manyik et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Sinn et al. U.S. Pat. No. 4,404,344 prepare methylaluminoxane by adding trimethyl aluminum to a slurry of $CuSO_4.5H_2O$ in toluene. Water as a metal hydrate controls its reactivity with the trimethyl aluminum. Kaminsky et al. U.S. Pat. No. 4,544,762 is similar except it uses an aluminum salt hydrate to supply the water. Likewise Welborn et al. U.S. Pat. No. 4,665,208 describe the use of other metal salt hydrates such as $FeSO_4.7H_2O$ as a water source in preparing aluminoxane.

Schoenthal et al. U.S. Pat. No. 4,730,071 show the preparation of methylaluminoxane by dispersing water in toluene using an ultrasonic bath to cause the dispersion and then adding a toluene solution of trimethyl aluminum to the dispersion. Schoenthal et al. U.S. Pat. No. 4,730,072 is similar except it uses a high speed, high shear-inducing impeller to form the water dispersion.

Edwards et al. U.S. Pat. No. 4,772,736 describe an aluminoxane process in which water is introduced below the surface of a solution of hydrocarbyl aluminum adjacent to a stirrer which serves to immediately disperse the water in the hydrocarbon solution.

SUMMARY

The present process prepares aluminoxane by flowing a thin falling film of a solution of an alkyl aluminum in an inert solvent down the inner wall of an upright hollow column while passing a water-wet inert gas up through the column causing the falling film of alkyl aluminum solution to contact the wet inert gas and react to form an alkyl aluminoxane solution which is washed down the inner column surface to a receiving vessel.

DESCRIPTION OF THE DRAWING

The drawing is a schematic depiction of the process not to scale using lines to represent piping.

DESCRIPTION OF THE PREFERRED EMBODIMENTS

A preferred embodiment of the invention is a process for making an alkylaluminoxane, said process comprising:

(A) forming a solution of alkyl aluminum compound in an inert solvent, (B) conducting said alkyl aluminum solution to the upper end of a vertical or inclined hollow column, (C) causing said alkyl aluminum solution to flow in a thin film down the inner surface of said vertical or inclined column, (D) contacting an inert gas with water to form a wet inert gas, (E) conducting said wet inert gas stream inside the lower end of said vertical or inclined column such that said wet inert gas passes upwardly in said vertical or inclined column and contacts said alkyl aluminum solution flowing down the inner surface of said vertical or inclined column and (F) collecting the effluent liquid at the bottom of said vertical or inclined column.

Any aluminum compound capable of reacting with water to form an aluminoxane can be used. This includes trialkyl aluminums, triaryl aluminums, mixed alkyl aryl aluminums, alkyl aluminum dihalides, dialkyl aluminum halides, alkylaluminum sesquihalides, dialkyl aluminum alkoxides and the like.

The preferred aluminum compounds are the hydrocarbyl aluminum compounds, especially trialkyl aluminum compounds such as trimethyl aluminum, triethyl aluminum, triisobutyl aluminum, tri-n-hexyl aluminum, tri-octyl aluminum and the like. Of these the more preferred are the tri-$C_{1-4}$-alkylaluminum compounds.

Of the various hydrocarbyl aluminoxanes, the more difficult to prepare are methylaluminoxane and ethylaluminoxane because of the extreme reactivity of trimethyl aluminum and triethyl aluminum with water. The most reactive is trimethyl aluminum and accordingly the most preferred embodiment is the application of the process to make methylaluminoxane.

Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compound in the inert solvent can range from about 1–30 weight percent. A preferred concentration is about 5–20 weight percent, more preferably 10–15 weight percent.

Operation of the process can be readily understood by referring to the drawing. Tank 1 is a container for an alkyl aluminum/inert solvent solution. Tank 1 is connected through conduit 2 and control valve 3 to annular reservoir 4 defined by column 5 which protrudes into and sealably engages closed housing 6. Housing 6 is vented through conduit 20 and pressure relief valve 21. Hollow column 5 is surrounded by cooling jacket 7 having coolant inlet 8 and outlet 9.

The bottom end of column 5 opens into vessel 10. Vessel 10 has an outlet conduit 12 through valve 13. Outlet conduit 12 is connected by conduit 14 through valve 16 and pump 17 back to annular reservoir 4.

Inert gas (nitrogen is used in the embodiment shown) tank 25 connects through conduit 26 and rotometer 28 to heated water tank 30 fitted with heating jacket 31. The top of water 31. The top of water tank 30 connects through conduit 32 to demister 33 fitted with heating jacket 34. The bottom of demister 33 connects through drain conduit 35 back to the bottom of water tank 30. Demister 33 is positioned above water tank 30 such that water cannot flow from water tank 30 to demister 33.

The top of demister 33 connects through conduit 40 and valve 41 to a centrally positioned outlet 45 inside the lower end of column 5. The upper end of column 5 opens into closed housing 6. Closed housing 6 is vented through conduit 20 and pressure relief valve 21 which is usually set to maintain about 1-20 psig in column 5.

In operation TMA/toluene solution from tank 1 flows through conduit 2 and control valve 3 into annular reservoir 4. The top of column 5 acts as a weir. When the TMA/toluene reaches the top of column 5 it flows over the weir and flows down the inside of column 5 in a thin film.

Nitrogen tank 25 delivers nitrogen at about 10 psig through conduit 26 and control valve 27 to the bottom of water tank 30. The water in tank 30 is heated to about 20°-50° C. Nitrogen bubbling up through water tank 30 becomes substantially saturated with water and is conducted through conduit 32 to demister 33. Any liquid water carried over drops to the bottom of demister 33 and is returned through conduit 35 to water tank 30.

Demister 33 is heated at least 5° C. and preferably at least 10° C. above the temperature in water tank 30 to prevent any condensation. The wet nitrogen is conducted through conduit 40 and control valve 41 to a central location inside the lower end of column 5. The wet nitrogen passes up through column 5 and contacts the falling film of TMA/toluene solution flowing down the inner surface of column 5. The water vapor reacts with the TMA forming methylaluminoxane (MAO) and evolving methane.

The mole ratio of water/TMA that actually react should be in the range of 1.0 to 2.0. Some of the water in the wet inert gas stream may pass through column 5 and be vented without reacting with TMA. Likewise some of the TMA may not react with water and be present in the final MAO solution as TMA. These quantities can be determined by analysis and the feed ratio of wet nitrogen and TMA solution adjusted accordingly such that the actual water/TMA reaction ratio falls in the desired 1.0–2.0 range.

Column 5 is cooled by passing coolant at about 0°–10° C. through cooling jacket 7. The toluene solution containing MAO passes down column 5 into vessel 10.

Although not essential, MAO solution from vessel 10 can be recycled via conduit 14, valve 16 and pump 17 back to reservoir 4 at the top of column 5. This serves to lower the amount of unreacted TMA in the final product solution. It also serves to flush any solids that may come out of solution in column 5 down into vessel 10.

Inert gas containing unreacted water and methane formed in the reaction of water with TMA passes through housing 6 and is vented through conduit 20 and pressure relief valve 21 which serves to maintain a small pressure (e.g. 1–20 psig) in the reaction system.

The MAO (or whatever other aluminoxane is made) solution in vessel 10 is removed through conduit 12 and valve 13. Aluminoxanes are very reactive with oxygen so should be stored under an inert atmosphere such as dry nitrogen. The MAO solution may be used directly to form an olefin polymerization catalyst or the solvent can be removed by evaporation to obtain a dry powder form of MAO. Spray drying of the aluminoxane solution has also been used to obtain a dry powder form of aluminoxane. In another mode of operation only part of the inert solvent is distilled out to obtain an aluminoxane concentrate. Any residual trialkyl aluminum in the product solution will co-distill with the solvent and remain in the distillate. This can be used to prepare trialkyl aluminum solution to be fed to the process from tank 1.

Before proceeding with a description of specific examples, the test used to evaluate the product will be described. MAO products made by various processes result in polymerization catalysts of different activity even though chemical analysis of the various products is very similar. This appears to be because of the different polymeric structures and molecular weights possible with MAO. Since the prime use of aluminoxanes is as a co-catalyst with a transitional metal compound in the polymerization of olefins, a measure of this property is the most important attribute of the aluminoxane.

The activity test used by applicants involves the preparation of a catalyst complex and the use of this complex in an actual polymerization. The test procedure is similar to the process described in Ishihara et al., U.S. Pat. No. 4,680,353, incorporated herein by reference. It involves the use of a titanium compound, e.g. titanium tetraethoxide, and an alkylaluminoxane, e.g. MAO, in the polymerization of styrene to form syndiotactic polystyrene.

EXAMPLES 1-5

These examples were conducted by passing a nitrogen stream at the rate shown in Table I through a water saturator maintained at the temperature and pressure shown in Table I. The wet $N_2$ was then passed through a demister vessel maintained at the indicated temperature and then into the lower end of a 1.0 inch dia. $\times$ 24 inch glass column. This glass column was jacketed so cold ethylene glycol/water could be passed through the jacket and cool the walls of the glass column.

A solution of TMA in toluene was fed to an annular reservoir surrounding the top of the glass column at the flow rate shown in Table I. This reservoir overflowed the top of the 1.0 in. glass column and flowed down the inner wall of the glass column into a product vessel.

Product solution was recycled to the reservoir at the top of the glass column at the rate shown in Table I. The product solution was withdrawn from the product flask at a continuous rate and analyzed for weight percent Al. The gas/Al ratio was also measured. The MAO solution was also subjected to the catalyst activity test. Results are included in the Table I.

TABLE I

| Example | TMA Feed Conc. | $N_2$ Flow cc/min | Saturator °C./psig | Demister Temp °C. | TMA Feed Rate ml/min |
|---|---|---|---|---|---|
| 1 | 5.0 | 14900 | 30/10 | 45 | 100 |
| 2 | 5.0 | 14900 | 30/10 | 45 | 50 |
| 3[1] | 10.0 | 12300 | 33/10 | 48 | 20 |
| 4 | 9.8 | 14400 | 35/10 | 60 | 50 |
| 5[1] | 10.0 | 13400 | 43/10 | 53 | 55 |

| Example | Recycle ml/min | Product ml/min | % Al | Gas/Al | Activity |
|---|---|---|---|---|---|
| 1 | 250 | 100 | 1.64 | 2.29 | 9.0 |
| 2 | 250 | 50 | 2.07 | 1.49 | 12.0 |
| 3 | 250 | 20 | 38.22[2] | 0.95[2] | 27.2 |
| 4 | 325 | 50 | 3.5 | 1.65 | 26.6 |
| 5 | 320 | 55 | 40.1[2] | 1.17[2] | 13.0 |

[1]Feed TMA was 10% TMA in Heptane.
[2]Analytical results are from the solids obtained by filtration.

The examples show that the falling film process can make an aluminoxane solution in a continuous process. When applied to making MAO from TMA the product solution exhibits a polymerization activity of at least 12 and the solid MAO shows an activity in excess of 26.

It should be understood that although trimethyl aluminum was used in the process description and in the examples, any alkyl aluminum compound can be used in the process to produce comparable results.

We claim:

1. A process for making an alkylaluminoxane, said process comprising:
   (A) forming a solution of alkyl aluminum compound in an inert solvent,
   (B) conducting said alkyl aluminum solution to the upper end of a vertical or inclined hollow column,
   (C) causing said alkyl aluminum solution to flow in a thin film down the inner surface of said vertical or inclined column,
   (D) contacting an inert gas with water to form a wet inert gas,
   (E) conducting said wet inert gas stream inside the lower end of said vertical or inclined column such that said wet inert gas passes upwardly in said vertical or inclined column and contacts said alkyl aluminum solution flowing down the inner surface of said vertical or inclined column and
   (F) collecting the effluent liquid at the bottom of said vertical or inclined column.

2. A process of claim 1 wherein said alkyl aluminum compound is a tri-$C_{1-8}$ alkyl aluminum.

3. A process of claim 2 wherein said alkyl aluminum compound is triisobutyl aluminum.

4. A process of claim 2 wherein said alkyl aluminum compound is trimethyl aluminum.

5. A process of claim 2 wherein said inert solvent is an aromatic hydrocarbon.

6. A process of claim 5 wherein said alkyl aluminum compound is triisobutyl aluminum.

7. A process of claim 5 wherein said alkyl aluminum compound is trimethyl aluminum.

8. A process of claim 5 wherein said aromatic hydrocarbon is toluene.

9. A process of claim 8 wherein said alkyl aluminum compound is triisobutyl aluminum.

10. A process of claim 8 wherein said alkyl aluminum compound is trimethyl aluminum.

11. A process of claim 1 wherein inert gas is nitrogen.

12. A process of claim 11 wherein said nitrogen is bubbled through water maintained at 20°–50° C. to form a substantially water saturated nitrogen stream.

13. A process of claim 12 wherein said saturated nitrogen stream is heated to a temperature above the temperature of said water while being conducted to said vertical or inclined columns to prevent condensation of water.

14. A process of claim 1 wherein said effluent liquid is collected in a vessel and about 10–90 percent of said effluent liquid is recirculated to said upper end of said vertical or inclined column and mixes with said alkyl aluminum solution.

15. A process of claim 14 wherein a portion of said effluent liquid is withdrawn from said vessel and not recirculated, said withdrawal being at a rate which maintains a substantially constant liquid level in said vessel.

16. A process of claim 14 wherein said inert solvent is an aromatic hydrocarbon and said solution is about 5–20 weight percent tri-$C_{1-8}$ alkyl aluminum.

17. A process of claim 16 wherein said aromatic hydrocarbon is toluene and said inert gas is nitrogen.

18. A process of claim 17 wherein said alkyl aluminum is triisobutyl aluminum.

19. A process of claim 17 wherein said alkyl aluminum is trimethyl aluminum.

* * * * *